US012617609B2

(12) United States Patent
Wang et al.

(10) Patent No.: US 12,617,609 B2
(45) Date of Patent: *May 5, 2026

(54) STERILIZATION AND DEODORIZATION WASTE CONTAINER HAVING DUAL-WAVE BAND ULTRAVIOLET LAMP TUBE

(71) Applicant: FUJIAN NASHIDA ELECTRONIC INCORPORATED COMPANY, Fujian (CN)

(72) Inventors: Shi Ping Wang, Fuzhou (CN); Jiangqun Chen, Fuzhou (CN); Youxi Lou, Fuzhou (CN); Zhou Lin, Fuzhou (CN)

(73) Assignees: Fujian Nashida Electronic Incorporated Company; Nine Stars Group (U.S.A.) Inc., Ontario, CA (US)

( * ) Notice: Subject to any disclaimer, the term of this patent is extended or adjusted under 35 U.S.C. 154(b) by 399 days.

This patent is subject to a terminal disclaimer.

(21) Appl. No.: 18/266,587

(22) PCT Filed: Jul. 30, 2021

(86) PCT No.: PCT/CN2021/109449
§ 371 (c)(1),
(2) Date: Jun. 9, 2023

(87) PCT Pub. No.: WO2022/121335
PCT Pub. Date: Jun. 16, 2022

(65) Prior Publication Data
US 2024/0100209 A1     Mar. 28, 2024

(30) Foreign Application Priority Data

Dec. 12, 2020    (CN) .......................... 202022965269.7

(51) Int. Cl.
B65F 7/00 (2006.01)
A61L 2/10 (2006.01)
(Continued)

(52) U.S. Cl.
CPC B65F 7/00 (2013.01); A61L 2/10 (2013.01); A61L 2/202 (2013.01); A61L 2/24 (2013.01);
(Continued)

(58) Field of Classification Search
CPC .... B65F 7/00; A61L 2/10; A61L 2/202; A61L 2/26; A61L 2202/11
See application file for complete search history.

(56) References Cited

U.S. PATENT DOCUMENTS

| | | | | | |
|---|---|---|---|---|---|
| 5,337,581 A | * | 8/1994 | Lott | ........................ | A61L 11/00 |
| | | | | | 422/292 |
| 6,365,113 B1 | * | 4/2002 | Roberts | ..................... | A61L 2/10 |
| | | | | | 422/186.3 |

(Continued)

FOREIGN PATENT DOCUMENTS

CN          110733785 A * 1/2020 ................ B65F 1/14

*Primary Examiner* — Jennifer Wecker
*Assistant Examiner* — Brady C Pilsbury
(74) *Attorney, Agent, or Firm* — David & Raymond Patent Firm; Raymond Y Chan

(57) ABSTRACT

A sterilization and deodorization waste container having dual-wave band ultraviolet lamp tube includes an isolation chamber provided on an inner side of a container lid and a dual-wave band ultraviolet lamp tube installed in the isolation chamber. The dual-wave band ultraviolet lamp tube is capable of simultaneously generating a direct ultraviolet light wave and an ozone ultraviolet light wave. The isolation chamber includes a reflector housing having a light transmitting window facing an inner cavity of a container body. The dual-wave band ultraviolet lamp tube is controlled by a control circuit to turn on to generate the ultraviolets into an (Continued)

inner cavity of the container body while the container lid is closed and to turn off to stop generating the ultraviolet while the container lid is opened.

13 Claims, 7 Drawing Sheets

(51) Int. Cl.

| | | |
|---|---|---|
| *A61L 2/20* | (2006.01) | |
| *A61L 2/202* | (2026.01) | |
| *A61L 2/24* | (2006.01) | |
| *B65F 1/02* | (2006.01) | |
| *B65F 1/16* | (2006.01) | |
| *A61L 103/00* | (2026.01) | |

(52) U.S. Cl.

CPC ............... *B65F 1/02* (2013.01); *B65F 1/163* (2013.01); *B65F 1/1646* (2013.01); *A61L 2103/23* (2026.01); *A61L 2202/11* (2013.01); *A61L 2202/121* (2013.01); *A61L 2202/122* (2013.01); *A61L 2202/14* (2013.01); *A61L 2202/15* (2013.01); *B65F 2210/129* (2013.01); *B65F 2210/168* (2013.01)

(56) References Cited

U.S. PATENT DOCUMENTS

| | | | | |
|---|---|---|---|---|
| 2007/0295355 A1* | 12/2007 | Ikuta | ................. | H01L 21/67115 |
| | | | | 134/1 |
| 2008/0175751 A1* | 7/2008 | Sun | ............................ | A61L 9/20 |
| | | | | 422/5 |
| 2008/0213128 A1* | 9/2008 | Rudy | ......................... | A61L 9/20 |
| | | | | 422/186.3 |
| 2011/0020184 A1* | 1/2011 | Sun | ............................ | A61L 2/10 |
| | | | | 422/114 |
| 2013/0078142 A1* | 3/2013 | Gordon | ..................... | A61L 2/10 |
| | | | | 220/660 |
| 2020/0390917 A1* | 12/2020 | Tang | ......................... | A61L 2/10 |

* cited by examiner

STERILIZATION AND DEODORIZATION WASTE CONTAINER HAVING DUAL-WAVE BAND ULTRAVIOLET LAMP TUBE

BACKGROUND OF THE PRESENT INVENTION

Field of Invention

The present invention relates to a sterilization and deodorization waste container, in particular a sterilization and deodorization waste container with dual-wave band ultraviolet lamp tube. The invention is adapted for waste containers with lids.

Description of Related Arts

Current household waste containers are generally equipped with lids configured to be opened by means of foot pedal, induction, gentle touch, and etc. In particular, in the waste container used in the kitchen, the kitchen waste disposed in the barrel is easy to breed bacteria and generate stinky smell, resulting in pollution of people's living environment. That further affects people's sense of smell and health and has health hazards. In order to solve the above problems, the current technology utilizes ultraviolet light wave for sterilization. That is, a direct ultraviolet lamp tube is installed in the waste container to sterilize the interior environment in the barrel, but this solution of using ultraviolet for direct sterilization has the following shortcomings:

1. The ultraviolet directly irradiated by ultraviolet lamp tube for sterilization can only propagate along a straight line, and thus there are more positions that cannot be irradiated and dead angles during the sterilization in the container. Therefore, its sterilization effect is relatively poor.
  2. In order to ensure light transmission and sterilization effect, the ultraviolet lamp tube in the current technology often adopts a naked installation method. That is, the ultraviolet lamp tube is arranged to face the interior of the container without obstruction. Due to the harsh environment within the container, the operating condition of the ultraviolet lamp tube is adversely affected directly, so that its service life span is also greatly shortened, the cost of use is high, and it is difficult to promote.

SUMMARY OF THE PRESENT INVENTION

In view of the shortcomings of the current technology, an objective of the invention is to provide a sterilization and deodorization waste container having dual-wave band ultraviolet lamp tube that avoids sterilization dead angle, enhances the sterilization effect, improves the operating environment of the ultraviolet lamp, improves service life span thereof, and reduces the cost of use.

According to the invention, the foregoing objective is attained by:

a sterilization and deodorization waste container having dual-wave band ultraviolet lamp tube, which includes a container body, a container lid and a control circuit, wherein one or more structural characteristic in further including an isolation chamber installed on an inner side of the container lid and a dual-wave band ultraviolet lamp tube arranged in the isolation chamber, the dual-wave band ultraviolet lamp tube being a lamp tube capable of simultaneously generating a direct sterilization ultraviolet light wave and an ozone sterilization ultraviolet light wave, the isolation chamber comprising a reflector housing and a transparent quartz glass, an opening of the reflector housing facing an inner cavity of the container body, shape and size of the transparent quartz glass fitting and matching to an opening surface of the reflector housing and being covered and connected to the opening of the reflector housing through a sealing silicone ring cover; a control input terminal of a driving circuit of the dual-wave band ultraviolet lamp tube being connected to a driving control terminal of the control circuit by a control switch.

Accordingly, the invention includes the following distinctive features:

1) By means of the isolation chamber provided to isolate with outside air, the dual-wave band ultraviolet lamp tube is sealingly contained between the reflector housing and the sealedly connected transparent quartz glass. Therefore, the glass surface may merely be wiped while it is dirty and the harsh environment in the waste container is prevented to affect the ultraviolet lamp tube in the isolation chamber, that optimizes the operating environment of the ultraviolet lamp tube, improves the service life span thereof and reduces the cost of use.

2) The transparent quartz glass is capable of enhancing a light transmittance of the ultraviolet light. The reflector housing can reflect most of the other ultraviolet light waves in the isolation chamber to penetrate through the transparent quartz glass into the container body, that greatly increases the intensity and number of effective light waves, and solves the conventional problems of light transmission and irradiation of the ultraviolet lamp tube.

3) The dual-wave band ultraviolet lamp tube provides double sterilizations, direct sterilization and ozone sterilization, wherein the ultraviolet light wave for direct sterilization has high photon energy to penetrate the cell membrane and nucleus of microorganisms, destroy the molecular bonds of their DNA, and kill them by making them lose replication ability or activity, and the ultraviolet light wave for ozone sterilization can turn O2 (oxygen) in the air into O3 (ozone) which has a strong oxidation effect that can diffuse in the container body and effectively kill bacteria. Ozone dispersion characteristics can just make up for the shortcomings of the ultraviolet for direct sterilization, including it only propagates along the straight line and the disinfection has dead angles. The two types of sterilization ultraviolet wave can sufficiently and effectively disinfect and sterilize the interior of the waste container, greatly improving the sterilization effect. In addition, during the disinfection and oxidation process, excess ozone will combine to become oxygen within 30 min to avoid ozone pollution.

4) The arrangement of the isolation chamber provides an excel environment for ozone sterilization of the ultraviolet light wave for ozone sterilization: Since ozone is highly corrosive, under the arrangement of the isolation chamber, ozone can only be diffused in the isolation chamber and the inner cavity of the container body, without affecting the electric circuit components and mechanical components within the interior space of the container lid.

In particular, the invention can further be embodied as follows:

The reflector housing is either a plastic electroplated member, or a resin shell body with a reflective film formed on inner side surfaces thereof, or a stainless steel made metal member with reflective arrangement on inner side surfaces thereof.

The reflector housing is preferred to be made of materials that are not easy to age, not easy to be corroded and oxidized, to avoid ozone corrosion and improve the reflection effect of light waves.

The ultraviolet light wave for direct sterilization is 240-280 nm ultraviolet light wave, preferably an ultraviolet light wave with a wavelength of 254 nm for direct sterilization.

The ultraviolet light wave for direct sterilization is also known as short-wave sterilization ultraviolet (UVC). The 253.7-254 nm wavelength ultraviolet light has the strongest photon energy and the best sterilization effect.

The ultraviolet light wave for ozone sterilization is 165-200 nm ultraviolet light wave, preferably an ultraviolet light wave with a wavelength of 185 nm for ozone sterilization.

The ultraviolet light wave (part of the UVD light wave) for ozone sterilization irradiated in the air can turn 02 (oxygen) in the air into 03 (ozone), wherein the 185 nm ozone sterilization ultraviolet light wave is the band with better effect.

The sealing silicone ring is a sealing ring having a cross-sectional inverted U-shape, such that a peripheral edge portion of the transparent quartz glass is positioned in an inner cavity of the U-shaped sealing ring, whereby the peripheral edge portion of the transparent quartz glass is completely covered in the sealing silicone ring.

The configuration of completely covering the peripheral edge of the transparent quartz glass can reduce damage caused by vibrations of the transparent quartz glass due to the vibration of the isolation chamber installed below the container lid while being flipped up and down frequently, so as to ensure the reliability of the structure. In addition, silicone can also prevent aging caused by ultraviolet radiation.

The control switch, which is either a Hall sensor, or an angle sensor, or a position limiting switch, comprises a control driving element and a detecting control element arranged in a separable manner, the control driving element being connected to the dual-wave band ultraviolet lamp tube and the control circuit.

For example, the control driving element of the angle sensor can be installed on a main rotating shaft of the container lid. When the container lid (or cover panel while the container lid is composed of a cover panel and a ring shape shell) opens at a certain angle (that is, when the container lid or cover panel is flipped up to open), the control circuit cuts off a power supply to the ultraviolet lamp tube while receiving a signal of the angle sensor and turns it off. When the container lid (or cover panel) is flipped down to close to a predetermined angle (when the container lid or cover panel is fully closed), the ultraviolet lamp tube is controlled to turn on for sterilization. For example, while the Hall sensor includes a Hall element as the control driving element and a magnet as the detecting control element, the ultraviolet lamp tube is turned off when the magnet leaves the detection range of the Hall element (i.e. when the container lid or cover panel is flipped up to open), and the ultraviolet lamp tube is turned on when the magnet enters the detection range of the Hall element (when the container lid or cover panel is flipped down to close). Accordingly, when the container lid or cover panel is opened, the control switch sends a signal and the control circuit controls the dual-wave band ultraviolet lamp tube to turn off to avoid ultraviolet from hurting human skin and eyes, and when the container lid or cover is closed, the control switch sends a signal to make the control circuit to timely turn on the ultraviolet lamp tube to sterilize the interior of the contain body in time.

One side of the container lid is pivotally connected with the container body, and a case is arranged at a hinging side of the container lid for receiving the control circuit. The case has a cavity provided therein and the insolation chamber is provided in the cavity. The control driving element and the detecting control element of the control switch are installed on the container lid and the container body respectively.

When the container lid and the container body are embodied as an inseparable connection structure, the isolation chamber is being flipped up and down with the container lid, so that the control switch is preferred to be installed on a side of the container lid or an open edge thereof.

The container lid comprises a ring shape shell and a cover panel. A side edge of the cover panel is hinged with the ring shape shell. The ring shape shell is sleeved to the container body, wherein a control circuit is installed in an inner cavity of the ring shall shell and the isolation chamber is arranged in a cavity provided in the ring shape shell; The control switch includes two sets, the control driving element and the detecting control element of one of the two sets are installed on the ring shape shell and the container body respectively, and the control driving element and the detecting control element of another set are installed on the cover panel and the ring shape shell respectively.

In normal use, the control switch can be triggered by flipping the cover panel up or down. When it is necessary to detach the ring shape shell from the container body, the control switch can also be triggered, so as to effectively avoid harmful to the human body caused by ultraviolet leakage.

In view of above, the invention provides a sterilization and deodorization waste container with dual-wave band ultraviolet lamp tube, which utilizes an isolation chamber with the reflector housing and the transparent quartz glass to install the dual-wave band ultraviolet lamp tube, that effectively improves the operating environment of the ultraviolet lamp tube while avoiding influence on the internal circuit and mechanical components outside the isolation chamber, improves the service life span and reduces the cost of use. The drawbacks of light transmission and irradiation of ultraviolet lamp tube are resolved. The double ultraviolet sterilizations can substantially and effectively disinfect and sterilize the waste container that greatly improves the sterilization effect.

Figure 1:
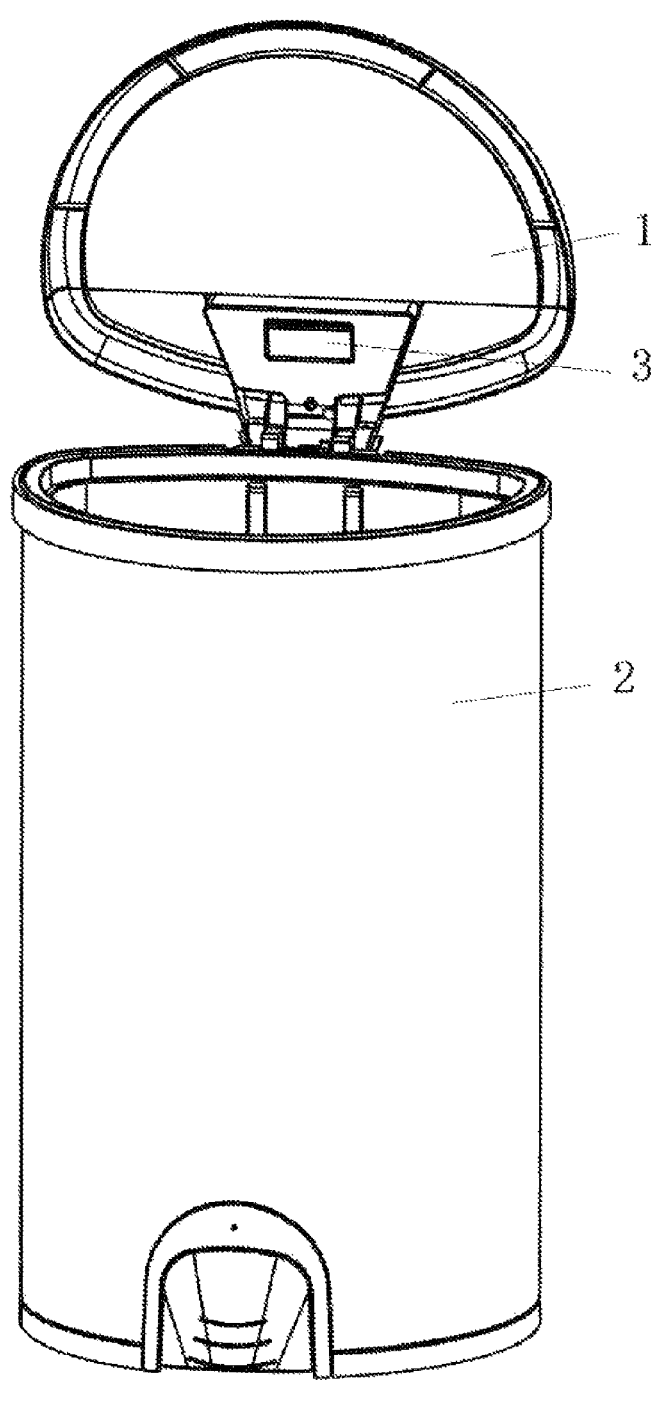
FIG. 1 is a structural perspective view of a sterilization and deodorization waste container having dual-wave band ultraviolet lamp tube according to a first embodiment of the invention.
Figure 2:
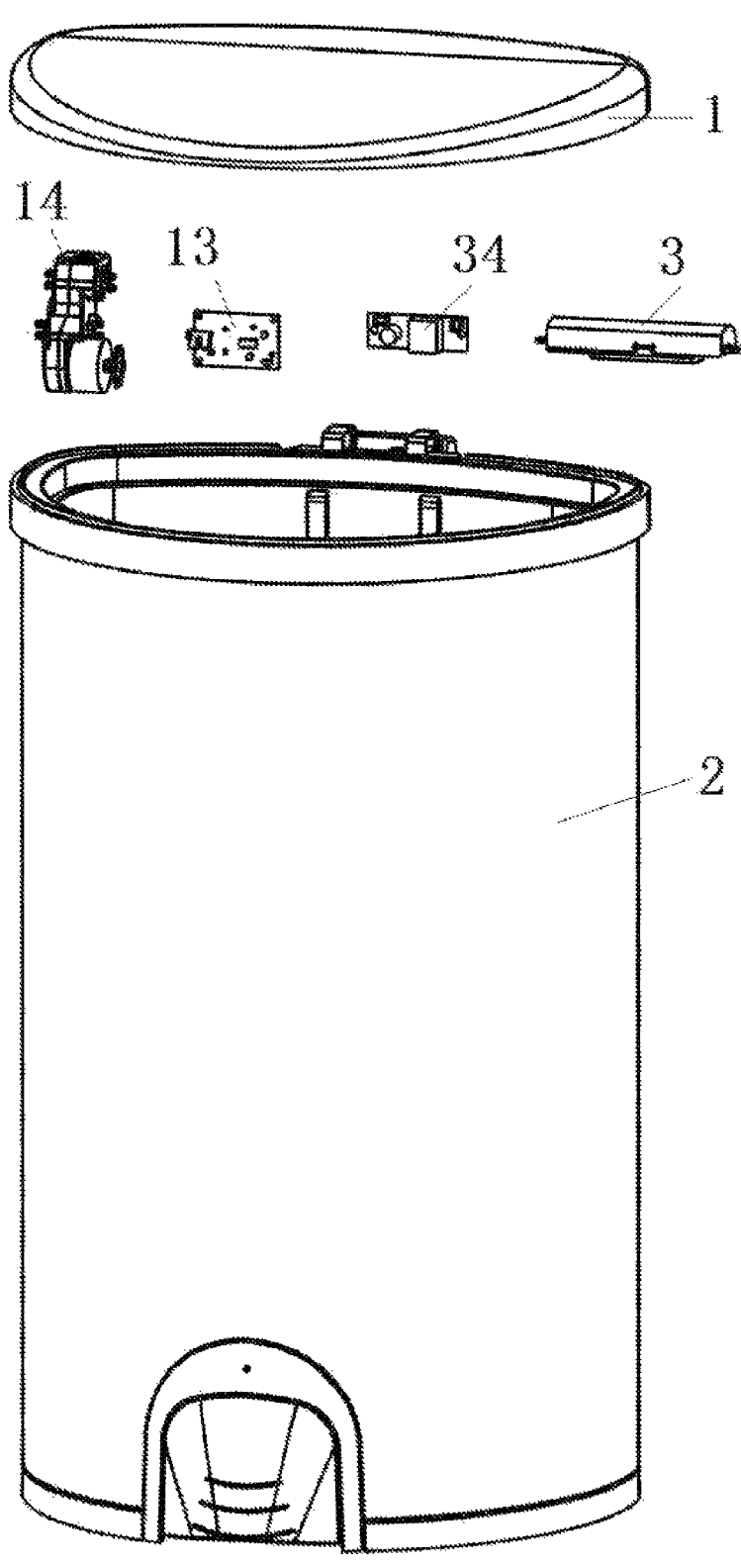

FIB. 2 is an exploded structural perspective view of the sterilization and deodorization waste container as shown in FIG. 1.

Figure 3:
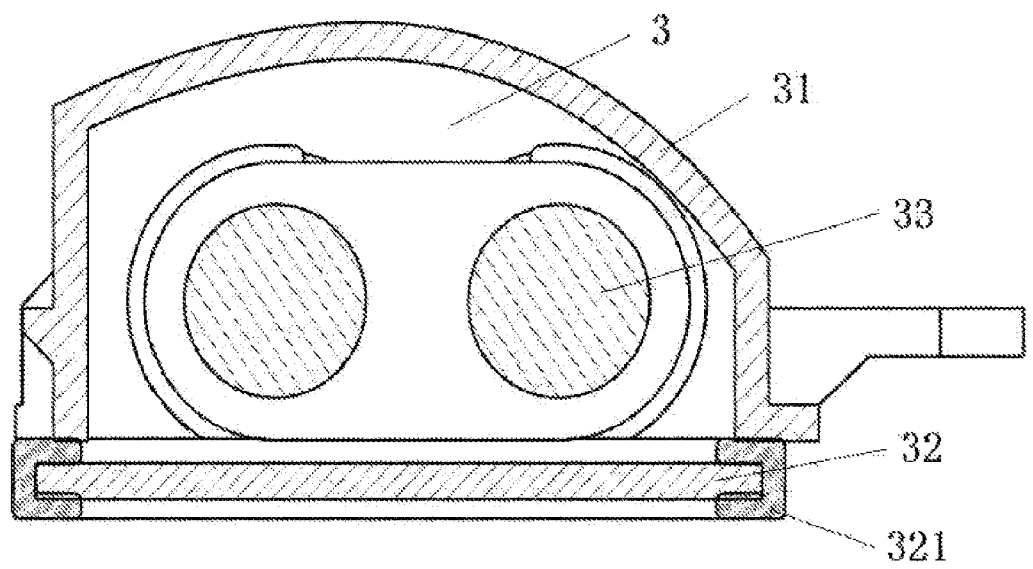

FIG. 3 is a structural sectional view of an isolation chamber of the sterilization and deodorization waste container having the dual-wave band ultraviolet lamp tube.

Figure 4:
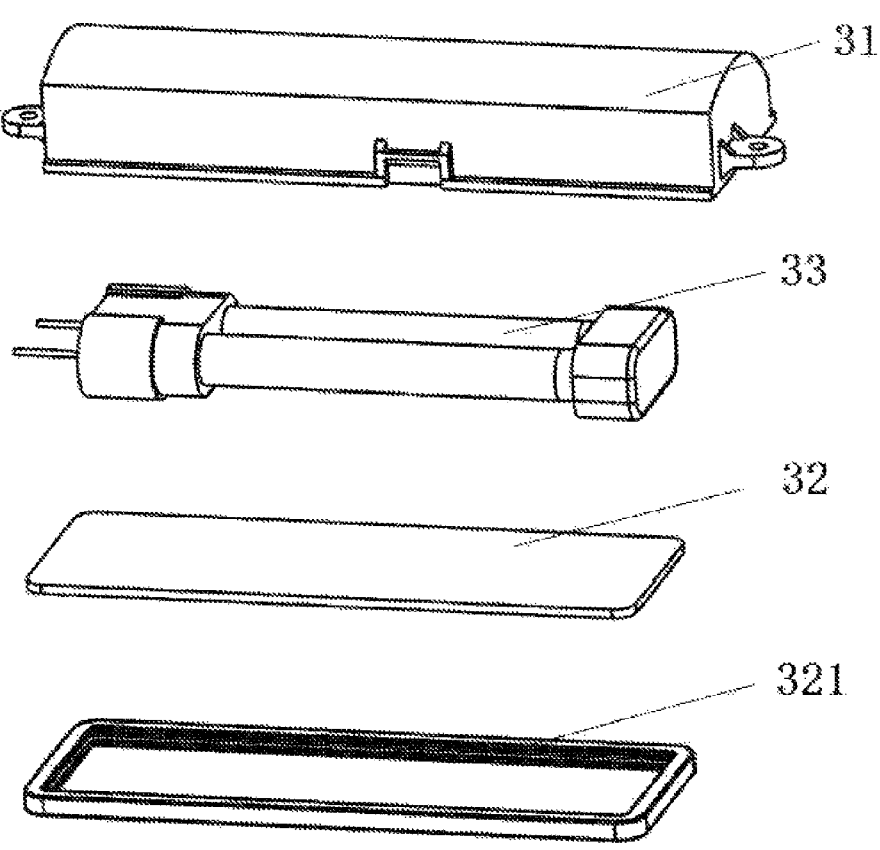

FIG. 4 is an exploded structural perspective view of the isolation chamber.

Figure 5:
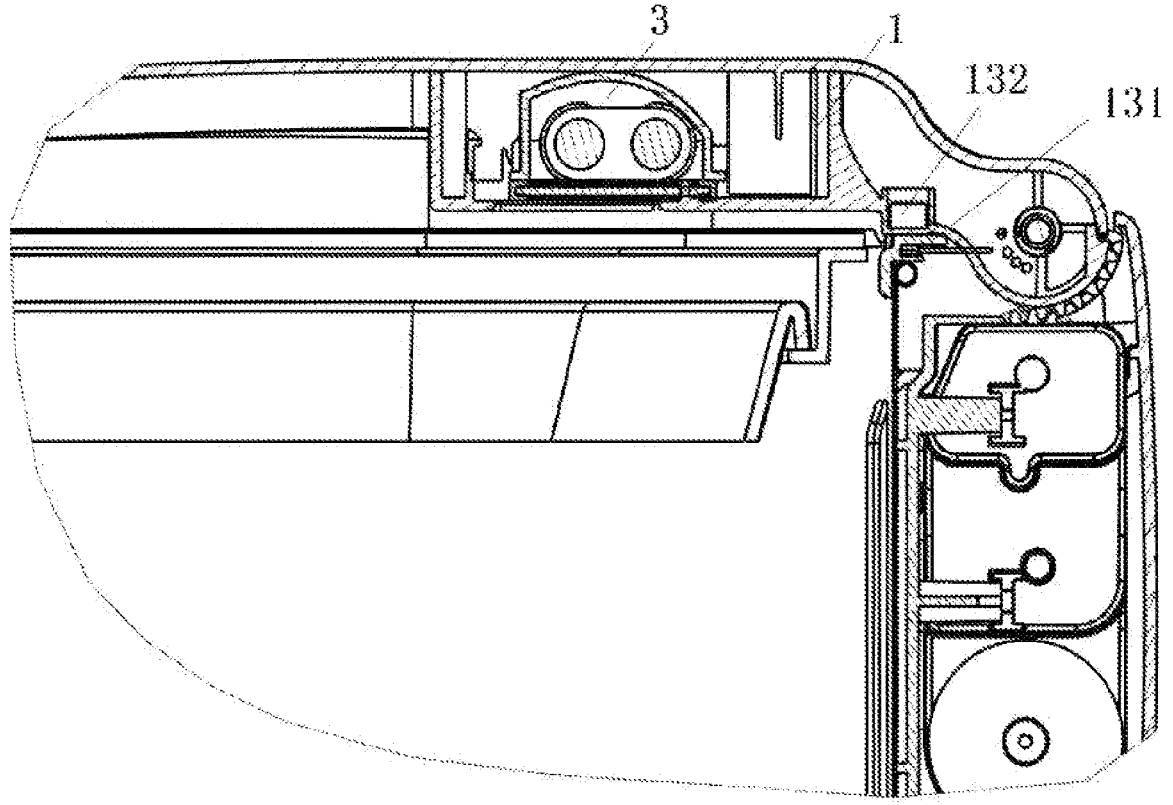

FIG. 5 is a partial structural sectional view of the sterilization and deodorization waste container with the dual-wave band ultraviolet lamp tube as shown in FIG. 1 according to the first embodiment of the invention.

Figure 6:
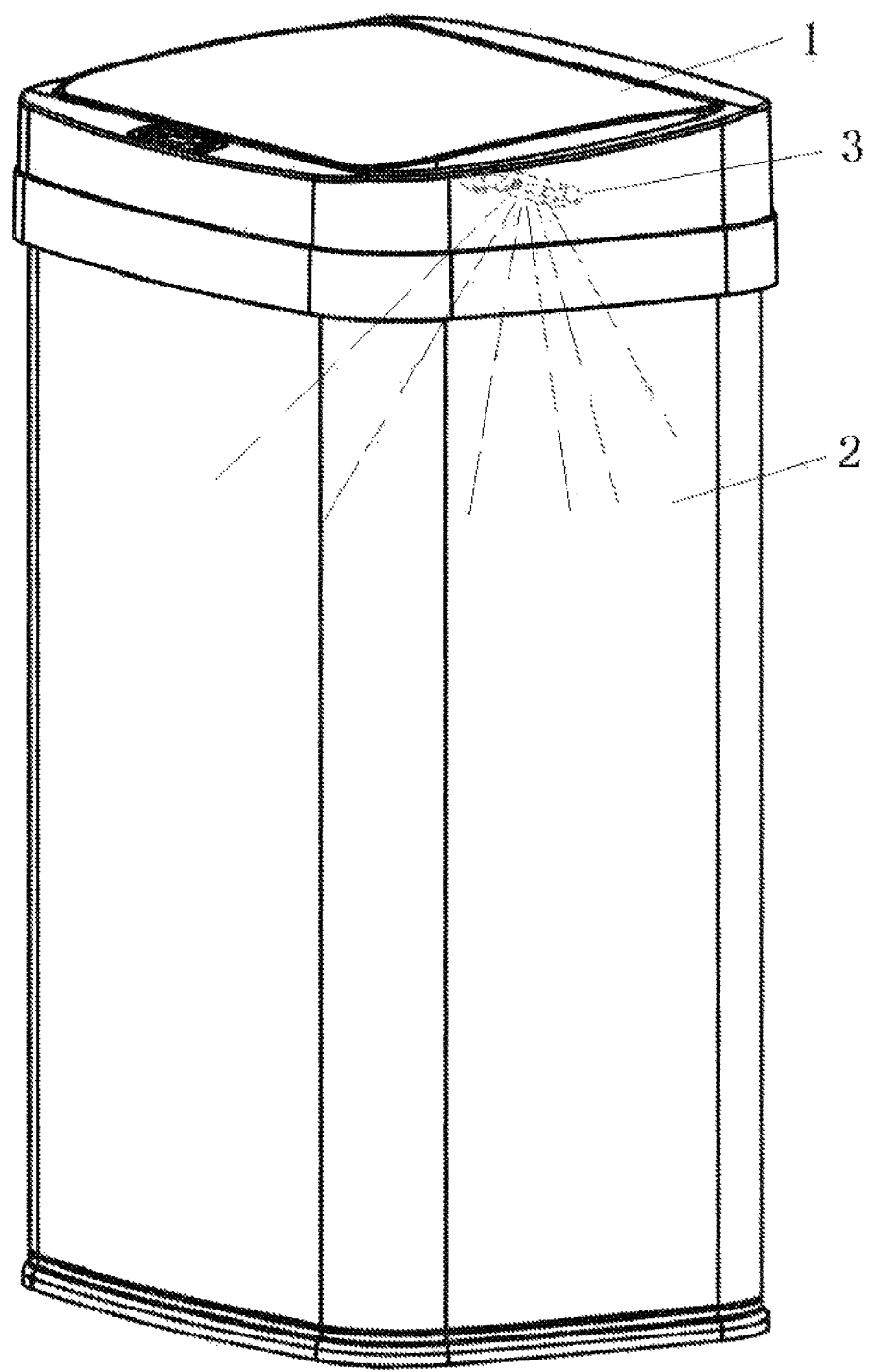

FIG. 6 is a perspective view of the sterilization and deodorization waste container with the dual-wave band ultraviolet lamp tube according to a second embodiment of the invention.

Figure 7:
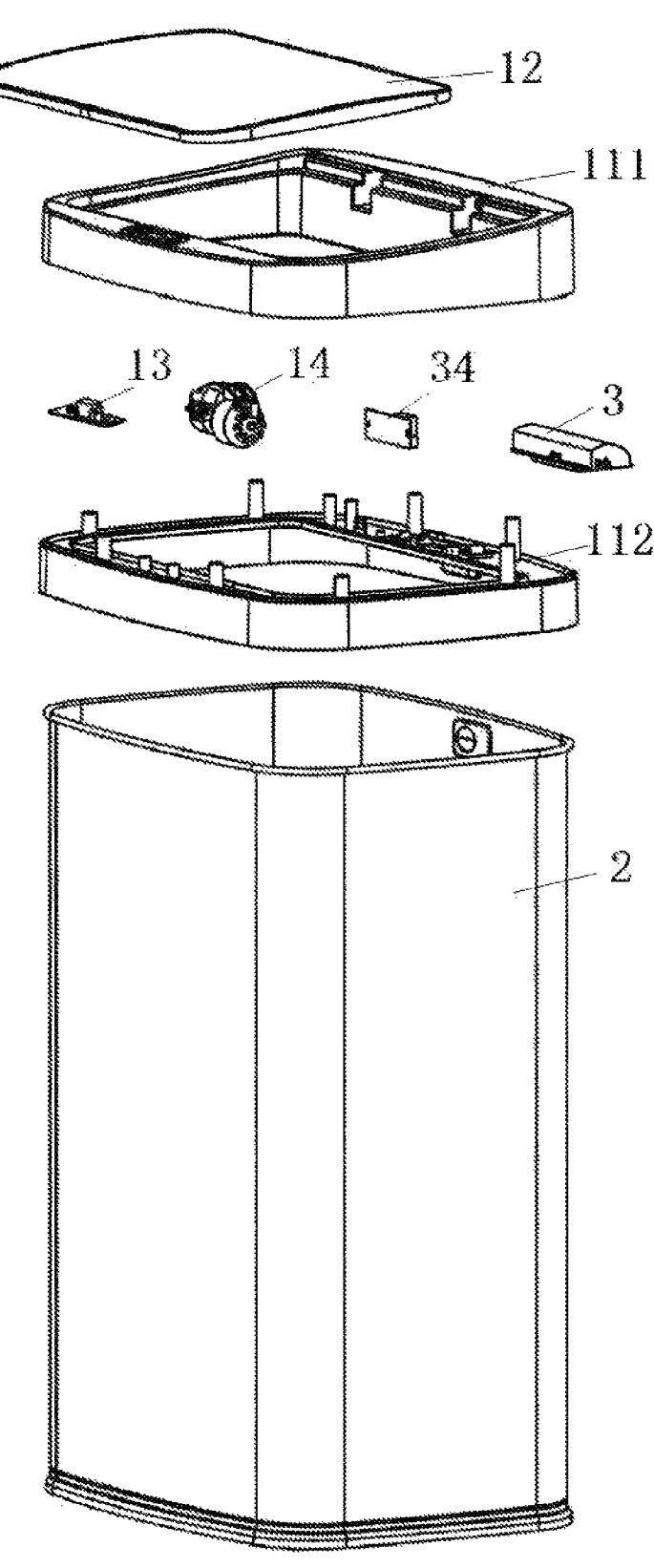

FIG. 7 an exploded structural perspective view of the sterilization and deodorization waste container as shown in FIG. 6.

Figure 8:
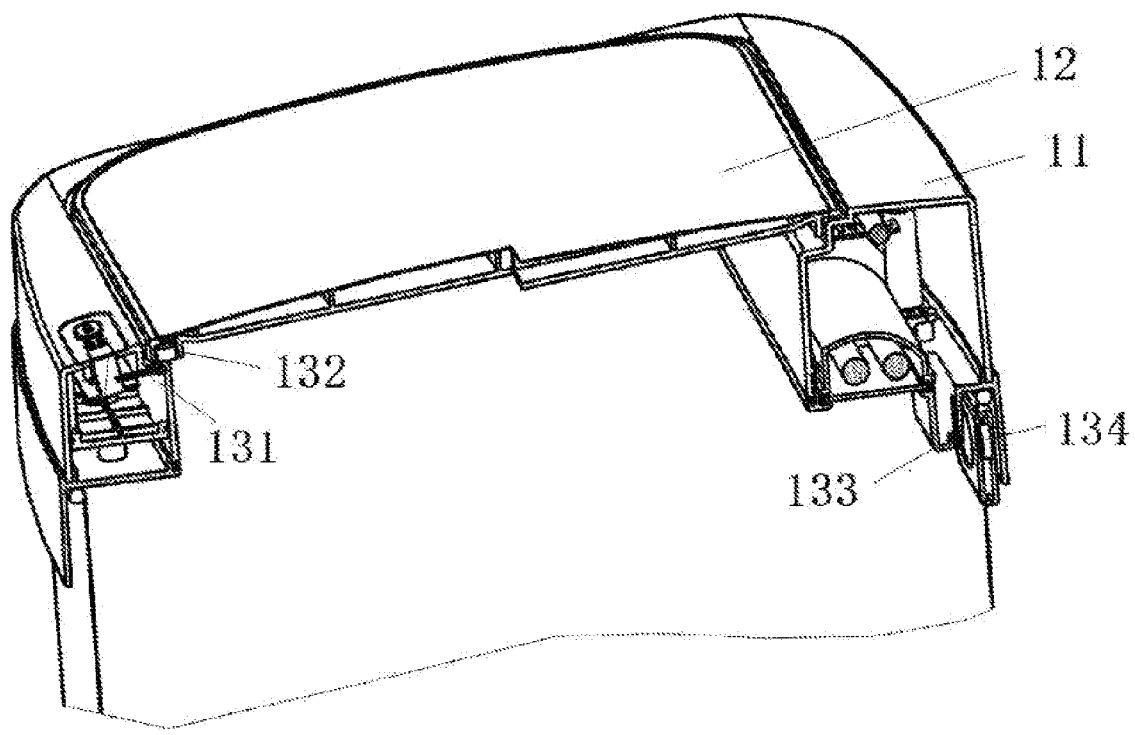

FIG. 8 is a partial structural sectional view of the sterilization and deodorization waste container with the dual-wave band ultraviolet lamp tube as shown in FIG. 6 according to the second embodiment of the invention.

DESCRIPTION OF THE REFERENCE NUMBERS IN THE DRAWING

1—Container Lid, 11—Ring Shape Shell, 111—Ring Shape Barrel Head, 112—Ring Shape Retainer Body, 12— Cover Panel, 13—Control Circuit, 131—Hall Element, 132—Magnet, 133—Hall Element, 134—Magnet, 14—Lid Opening and Closing Driving Device, 2—Container Body, 3—Isolation chamber, 31—Reflector Housing, 32—Transparent Quartz Glass, 321—Sealing Silicone Ring, 33—Dual-Wave Band Ultraviolet Lamp Tube, 34—Ultraviolet Lamp Tube Driver Circuit.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

First Preferred Embodiment

This embodiment is a sterilization and deodorization waste container having dual-wave band ultraviolet lamp tube, while its container lid is not separable from its container body (such as foot-step waste container, foot-touch waste container, and etc., the present embodiment referring to the foot-touch waste container), the configurations of the foot touch control and the opening and closing operation of the container lid are conventional art that is not repeatedly described in the first embodiment. Please referring to FIG. 1 to FIG. 5:

A sterilization and deodorization waste container having a dual-wave band ultraviolet lamp tube includes a container lid 1, a container body 2 and a control circuit 13, the container body 2 being adapted for storing waste. The container lid 1 is pivotally connected at an opening above the container body 2, and the control circuit 2 and a lid opening and closing driving device 14 are installed to the container body 13. An isolation chamber 3 isolated from the air outside is arranged below the container lid 1. A light-transmitting widow is formed below the isolation chamber 3. Due to the harsh environment of the waste container, the dual-wave band ultraviolet lamp tube 33, having a II shaped configuration, is arranged in the air-isolated isolation chamber 3 and, since the ultraviolet light penetration ability is extremely weak, a transparent quartz glass 32 having very high light transmittance is embodied as the light-transmitting widow of the isolation chamber 3. The dual-wave band ultraviolet lamp tube 33 produces ultraviolet light waves, with 254 nm wavelength and 185 nm wavelength, irradiated into the waste container through the light-transmitting window made of the transparent quartz glass 32, so as to use the ultraviolet light waves for sterilization and deodorization. In which, the ultraviolet light wave with 254 nm wavelength (also known as short-wave sterilization ultraviolet) has a higher photon energy, that can penetrate cell membranes and nucleus of microorganisms, destroy the molecular bonds of their DNA, and make them losing replication ability or activity and die while irradiating microorganisms. Also, the irradiating of the ultraviolet light wave with 185 nm wavelength in the air can turn 02 (oxygen) in the air into $O_3$ (ozone). Ozone, which has a strong oxidation effect, can effectively kill bacteria. The diffusion and dispersion ability of ozone fitly make up for the shortcoming of ultraviolet that only propagates along a straight line and has dead angles and corners for disinfection, such that the function of sterilization and deodorization is strengthened.

The isolation chamber 3 is comprised of a reflector housing 31, the transparent quartz glass 32 and a sealing silicone ring 321. A peripheral edge portion of the transparent quartz glass 32 is affixed with the sealing silicone ring 321 which has a "U" shaped cross section to protect. The dual-wave band ultraviolet lamp tube 33 is arranged in the sealed isolation chamber 31 configured by the reflector housing 31 and the transparent quartz glass 32. Since ultraviolet has a strong aging ability and ozone is very corrosive, the dual-wave band ultraviolet lamp tube 33 is enclosed in the sealed isolation chamber 3, such that, on one hand, the ultraviolet light wave avoids irradiating plastic structural components of a driving control mechanism but concentrates in positions of the waste contained in the container body and, on the other hand, the ozone generated by the ultraviolet light wave irradiation does not be dispersed into an inner space of the container lid 1, causing the control circuit and the internal structural components to be corroded and oxidized by the ozone. At the same time, the dual-wave band ultraviolet lamp tube 33 is isolated and protected from being polluted. If the light-transmitting window is soiled, it merely needs to wipe the transparent quartz glass 32 to ensure sufficient ultraviolet light irradiation. The reflector housing 31 (the reflector housing 31 may be made of materials such as electroplated plastic member, a reflective filmed or a stainless steel made metal member and other materials that are not easy to age, not easy to be corroded and oxidized, the reflector housing 31 in the present embodiment referring to an electroplated plastic member) is configured to reflect ultraviolet light waves into the waste container, which greatly increases the effective light wave intensity. The ultraviolet light waves reflected through the reflector housing 31 can only be irradiated into the waste container through the transparent quartz glass 32. The transparent quartz glass 32 is capable of transmitting most of the ultraviolet light waves with 254 nm wavelength and 185 nm wavelength, that ensures most of the ultraviolets being irradiated into the waste container for sterilization and generating ozone for sterilization and deodorization in the waste container. Since silicone has strong anti-aging ability, the sealing silicone ring 321 of the present embodiment adopts a sealing silicone with a "U" shaped cross-section.

The container lid 1 is configured to be inseparable from the container body 2. A control switch is installed in the container body 2 (this control switch can be a Hall element, a position limiting switch, an angle sensor, and etc., the present embodiment utilizing a Hall element, that is, the Hall element 131). A magnet 132 is installed to the container lid 1 such that when the container lid 1 is flipped up to open, the magnet 132 leaves a detection range of the Hall element 131 with the container lid 131, the control circuit 13 receives a signal sent from the Hall element 131, and the dual-wave band ultraviolet lamp tube 33 is turned off by a ultraviolet lamp tube driver circuit 34 to cease the generation of the ultraviolets to prevent causing harm to human skin and eyes. When the container lid 1 is flipped down to close in place, the Hall element 131 detects an approaching of the magnet 132 and the control circuit 13 controls the dual-wave band ultraviolet lamp tube 33 to turn on, or otherwise, the dual-wave band ultraviolet lamp tube 33 is always remained in a turn-off state.

The parts not described in the first embodiment are the same as the conventional art.

Second Preferred Embodiment

The present embodiment is a sterilization and deodorization induction waste container having dual-wave band ultraviolet lamp tube, while its container lid is no separable from its container body (such as induction waste container, the present embodiment referring to an induction waste container), the configurations of the infrared sensing component and the opening and closing operation of the container lid are conventional art that is not repeatedly described here. Referring to FIGS. 3, 4 and 6-8, a sterilization and deodorization waste container having a dual-wave band ultraviolet lamp tube includes a container lid 1, a container body 2 and a control circuit 13, the container body 2 being used to store waste. The container lid 1 includes a ring shape shell 11 (the ring shape shell 11 is comprised of a ring shape barrel head 111 and a ring shape retainer body 122) and a cover panel 12. The cover panel 12 is pivotally connected to the ring shape shell 11. The container lid 1 is placed above an opening of the container body 2. The control circuit 13 and the lid opening and closing driving device 14 are installed in a receiving cavity of the ring shape shell 11 defined after the ring shape barrel head 111 and the ring shape retainer body 112 are affixed together. An isolation chamber 33 isolated from the air outside is arranged below the container lid 1. A dual-wave band ultraviolet lamp tube 3 is installed in the isolation chamber 33. A transparent quartz glass 33 with very high light transmittance is provided below the dual-wave band ultraviolet lamp tube 33 as a light-transmitting window. The dual-wave band ultraviolet lamp tube 33 is generate ultraviolets with a254 nm wavelength and a 185 nm wavelength which irradiate into the waste container through the transparent quartz glass 32 of the light-transmitting window to process sterilization and deodorization through the ultraviolet light waves, wherein the ultraviolet light wave with 185 nm wavelength can produce ozone for sterilization and deodorization. In addition, due to the dispersion and diffusion ability of ozone, the ozone fills the interior space of the waste container that fitly makes up for the shortcoming of ultraviolet that only propagates along a straight line and has dead angles and corners for disinfection, such that the function of sterilization and deodorization is strengthened.

The configurations and material selections of the isolation chamber 3, the reflector housing 31, the transparent quartz glass 32, the sealing silicone ring 321, the dual-wave band ultraviolet lamp tube 33 and the sterilization and deodorization principle of the dual-wave band ultraviolet lamp tube 33 may refer to the description in the first preferred embodiment and are not repeatedly described in this embodiment.

The container lid 1 may be separated from the container body 2. The container lid 1 is comprised of a ring shape shell 11 and a cover panel 12. A control switch is installed on the container lid 1 (this control switch can be a Hall element, a position limiting switch, an angle sensor, and etc., this embodiment utilizing Hall elements, including a Hall element 131 and a Hall element 133). A magnet 134 is installed on the container body 134 such that, when the container lid 1 is separated from the container body 2, the magnet 134 leaves a detection range of the Hall element 133. After the Hall element 133 generates a signal, the control circuit 13 controls the dual-wave band ultraviolet lamp tube 33 to turn off to stop generating the ultraviolets to prevent causing harm to human skin and eyes. Similarly, the cover panel 12 is equipped with a magnet 132 such that, when the cover panel 12 is opened, the magnet 132 leaves the detection range of the Hall element 131. After the Hall element 131 generates a signal, the control circuit 13 controls the dual-wave band ultraviolet lamp tube 33 to turn off to stop generating the ultraviolets to prevent causing harm to human skin and eyes. When the cover panel 12 is closed in place and the container lid 1 is placed on the container body 2, that is only while these two conditions are met at the same time, the control circuit 13 controls the dual-wave band ultraviolet lamp tube 33 to turn on and operate, or otherwise, the dual-wave band ultraviolet lamp tube 33 is always remained in the turn-off state. Based on the embodiments described above, the ultraviolet lamp tube 33 can also be set with a predetermined sterilization time period.

The parts not described in the second embodiment are the same as the conventional art.

The above description is merely preferred embodiments of the invention and is not intent to limit the invention, and any modification, equivalent substitution, improvement, and etc. made within the spirit and principles of the invention should be included within the scope of the claimed invention.

What is claimed is:

1. A sterilization and deodorization waste container with dual-wave band ultraviolet lamp tube, including:
   a container body having an inner cavity,
   a container lid pivotally connected to the container body,
   a dual-wave band ultraviolet lamp tube installed in an isolation chamber and configured to simultaneously generate ultraviolets, including a direct sterilization ultraviolet light wave and an ozone sterilization ultraviolet light wave at the same time,
   the isolation chamber, which is provided on an inner side of the container lid, including a reflector housing and a transparent quartz glass, an opening of the reflector housing facing the inner cavity of the container body, the transparent quartz glass having a shape and a size fitly matching with an opening surface of the reflector housing and being connected to and covering to the opening of the reflector housing through a sealing the silicone ring, and
   a control circuit configured to selectively control the dual-wave band ultraviolet lamp tube to turn off to stop generating the ultraviolets while the container lid is opened and to turn on to generate the ultraviolets while the container lid is closed.

2. The sterilization and deodorization waste container, as recited in claim 1, wherein the reflector housing is selected from a group consisting of either an electroplated plastic member, a resin shell body with a reflective film formed on inner side surfaces, er and a stainless steel made metal member with a reflective arrangement on inner side surfaces thereof.

3. The sterilization and deodorization waste container, as recited in claim 1, wherein the direct sterilization ultraviolet light wave has a wavelength between 240 nm to 280 nm.

4. The sterilization and deodorization waste container, as recited in claim 1, wherein the ozone sterilization ultraviolet light wave has a wavelength between 165 nm to 200 nm.

5. The sterilization and deodorization waste container, as recited in claim 1, wherein the sealing silicone ring has a "U" shaped cross-section and a peripheral edge portion of the transparent quartz glass is positioned in an inner groove of the U-shaped sealing silicone ring, such that the peripheral edge portion of the transparent quartz glass is fully covered in the sealing silicone ring.

6. The sterilization and deodorization waste container, as recited in claim 1, further comprising a control switch, which is selected from a group consisting of a Hall sensor, an angle sensor, and a position limiting switch, comprising a control driving element and a detecting control element arranged in a separable manner, the control driving element being connected to the dual-band ultraviolet lamp tube and the control circuit.

7. The sterilization and deodorization waste container, as recited in claim 1, wherein one side of the container lid is pivotally hinged to the container body and a housing is provided at the side of the container lid, the housing having a cavity, the isolation chamber being provided in the cavity, a control driving element and a detecting control element of a control switch are installed on the container lid and the container body respectively.

8. The sterilization and deodorization waste container, as recited in claim 1, wherein the container lid comprises a ring shape shell and a cover panel, one side of the cover panel being pivotally connected to the ring shape shell, the ring shape shell being sleeved to the container body, the control circuit being installed in an inner cavity of the ring shape shell, the isolation chamber being provided in a cavity of the ring shape shell, wherein a control driving element and a detecting control element of a first control switch are installed on the ring shape shell and container body respectively, wherein a control driving element and a detecting control element of a second control switch are installed on the cover plate and the ring shape shell respectively.

9. The sterilization and deodorization waste container, as recited in claim 3, wherein the direct sterilization ultraviolet light wave has a wavelength of 254 nm.

10. The sterilization and deodorization waste container, as recited in claim 4, wherein the ozone sterilization ultraviolet light wave has a wavelength of 185 nm.

11. A sterilization and deodorization waste container, comprising:

a container body having an inner cavity for storing a waste and a container opening;

a container lid covering the container opening of the container body;

an isolation chamber, provided on an inner side of the container lid and isolated from air outside, comprising a reflector housing having an opening facing the container cavity and a light-transmitting window sealingly covering the opening of the reflector housing;

a dual-wave band ultraviolet lamp tube installed in the isolation chamber and configured to generate ultraviolets, including a direct sterilization ultraviolet light wave having a wavelength between 240 nm to 280 nm and an ozone sterilization ultraviolet light wave having a wavelength between 165 nm to 200 nm, wherein a portion of the ultraviolets directly irradiates into the inner cavity of the container body through the light-transmitting window and a portion of the ultraviolets is reflected by the reflector housing to irradiate into the inner cavity of the container body through the light-transmitting window; and a control circuit configured to selectively turn on the dual-wave band ultraviolet lamp tube to generate the ultraviolets while the container lid is closed with respect to the container body and turn off the dual-wave band ultraviolet lamp tube to stop generating the ultraviolets while the container lid is opened with respect to the container body;

wherein the container lid comprises a ring shape shell arranged to cover the container opening of the container body and a cover panel pivotally connected to the ring shape shell, wherein the control circuit comprises two pairs of detecting control element and driving control element, wherein the two detecting control elements are installed on the ring shape shell and the two driving control elements are installed on the container body and the cover panel respectively, such that when one of the detecting control elements leaves the corresponding driving control element while either the cover panel or the ring shape shell is opened with respect to the container body, the control circuit controls the dual-wave band ultraviolet lamp tube to turn off to stop generating the ultraviolets, and that when both the ring shape shell and the cover panel are closed in place with respect to the container body, the detecting control elements detect an approaching of the corresponding control driving element and the control circuit controls the dual-wave band ultraviolet lamp tube to turn on to generate the ultraviolets.

12. A sterilization and deodorization waste container comprising:

a container body having an inner cavity for storing a waste and a container opening;

a container lid covering the container opening of the container body;

an isolation chamber, provided on an inner side of the container lid and isolated from air outside, comprising a reflector housing having an opening facing the container cavity and a light-transmitting window sealingly covering the opening of the reflector housing, wherein the light-transmitting window comprises a transparent quartz glass fitly and sealedly mounted to the opening of the reflector housing;

a dual-wave band ultraviolet lamp tube installed in the isolation chamber and configured to generate ultraviolets, including a direct sterilization ultraviolet light wave having a wavelength between 240 nm to 280 nm and an ozone sterilization ultraviolet light wave having a wavelength between 165 nm to 200 nm, wherein a portion of the ultraviolets directly irradiates into the inner cavity of the container body through the light-transmitting window and a portion of the ultraviolets is reflected by the reflector housing to irradiate into the inner cavity of the container body through the light-transmitting window; and a control circuit configured to selectively turn on the dual-wave band ultraviolet lamp tube to generate the ultraviolets while the container lid is closed with respect to the container body and turn off the dual-wave band ultraviolet lamp tube to stop generating the ultra-violets while the container lid is opened with respect to the container body;

wherein the container lid comprises a ring shape shell arranged to cover the container opening of the container body and a cover panel pivotally connected to the ring shape shell, wherein the control circuit comprises two pairs of detecting control element and driving control element, wherein the two detecting control elements are installed on the ring shape shell and the two driving control elements are installed on the container body and the cover panel respectively, such that when one of the detecting control elements leaves the corresponding driving control element while either the cover panel or the ring shape shell is opened with respect to the container body, the control circuit controls the dual-wave band ultraviolet lamp tube to turn off to stop generating the ultraviolets, and that when both the ring shape shell and the cover panel are closed in place with respect to the container body, the detecting control elements detect an approaching of the corresponding control driving element and the control circuit controls the dual-wave band ultraviolet lamp tube to turn on to generate the ultraviolet.

13. The sterilization and deodorization waste container, as recited in claim 12, wherein each of the detecting control elements is selected from a group consisting of Hall element, position limiting switch and an angle sensor and the control driving element is a magnet.

* * * * *